United States Patent [19]

van Koutrik et al.

[11] Patent Number: 5,948,422
[45] Date of Patent: Sep. 7, 1999

[54] ORAL DOSAGE-FORMS CONTAINING A β-LACTAM ANTIBIOTIC

[75] Inventors: Robertus Cornelis van Koutrik, Leiderdorp; Gerrit-Jan Sijbrands, Zandvoort, both of Netherlands

[73] Assignee: Yamanouchi Europe B.V., Leiderdorp, Netherlands

[21] Appl. No.: 08/894,602

[22] PCT Filed: Feb. 8, 1996

[86] PCT No.: PCT/EP96/00547

§ 371 Date: Aug. 6, 1997

§ 102(e) Date: Aug. 6, 1997

[87] PCT Pub. No.: WO96/24337

PCT Pub. Date: Aug. 15, 1996

[30] Foreign Application Priority Data

Feb. 8, 1995 [EP] European Pat. Off. .............. 95200313

[51] Int. Cl.⁶ .................................................... A01N 25/12
[52] U.S. Cl. ...................... 424/408; 424/465; 424/489; 514/198; 514/199; 514/200
[58] Field of Search ................... 424/452, 465, 424/489; 514/196, 197, 198, 199, 200

[56] References Cited

U.S. PATENT DOCUMENTS

| | | | |
|---|---|---|---|
| 3,344,030 | 9/1967 | Stevens et al. | 424/465 |
| 5,049,394 | 9/1991 | Howard et al. | 424/490 |
| 5,605,889 | 2/1997 | Curatolo et al. | 514/29 |
| 5,643,591 | 7/1997 | Mehra et al. | 424/408 |
| 5,725,854 | 3/1998 | Sherwood et al. | 424/489 |

FOREIGN PATENT DOCUMENTS 0281200  9/1988  European Pat. Off. .

*Primary Examiner*—Neil S. Levy
*Attorney, Agent, or Firm*—McDonnell Boehnen Hulbert & Berghoff

[57] ABSTRACT

A granulate, containing at least 50 wt. % of a water soluble β-lactam antibiotic, is provided. A process to prepare a granulate containing such β-lactam antibiotic comprises moistening components making up the granulate with an aqueous solution containing no substantial amount of a wet granulation binding agent. Oral dosage-forms, which contain the said antibiotic in a granular form, a cellulose product and a disintegrant and which quickly disperse when placed in an aqueous environment, are disclosed, as well as a method for the preparation of the dosage-forms.

3 Claims, No Drawings

ORAL DOSAGE-FORMS CONTAINING A β-LACTAM ANTIBIOTIC

This application is a 371 of PCT/EP96/00547, filed Feb. 8, 1996.

The present invention relates to quickly dispersible dosage-forms for oral administration, containing a water soluble β-lactam antibiotic, and the preparation thereof.

BACKGROUND OF THE INVENTION

β-lactam antibiotics are widely used in the treatment of all kinds of bacterial infections. Representatives of the different groups (penicillins, cephalosporins etc.) of the said antibiotics have shown to be active or oral administration. Although an anhydrous form, hydrates, solvates, salts and esters of the β-lactam antibiotics have been prepared, large differences in stability between the various forms of those antibiotics have been observed. For this reason flucloxacillin is commercially available only as the sodium salt, the anhydrous form of ampicillin is most preferred and the form of amoxicillin currently in use if the trihydrate. On the other hand other β-lactam antibiotics have appeared to be stable in more than one form: e.g. phenoxymethylpenicillin is commercially available as the free acid, as various salts (calcium, sodium, potassium) and as an ester. However, on oral administration only the potassium salt has shown the best bioavailability. A person, who has to prepare a pharmaceutical dosage-form, containing a β-lactam antibiotic, thus cannot always avail of that chemical form, which he would prefer in view of solubility and organoleptic properties.

Generally, if a quick onset of action of a drug from a solid dosage-form, such as a tablet, is aimed at, the composition and the manufacturing method of such tablet will be carefully selected as to enable a fast disintegration of the tablet and a dissolution of the drug, when placed in an aqueous environment. EP-B-0200281 discloses fast-disintegrating tablets, containing an amphoteric β-lactam antibiotic, 24–70 wt % of a first disintegrant, which may be microcrystalline cellulose, and a second disintegrant. The tablets are prepared by making a wet granulate, comprising the antibiotic compound without using a substantial amount of a wet granulation binding agent, blending the granulate with the disintegrants and other excipients and compressing the tabletting mixture. EP-B-0330284 discloses a process for the preparation of a pharmaceutical granulate by granulating a drug having a solubility in water of less than 10 wt % and 20–100 wt % of microcrystalline cellulose with water without using a substantial amount of a wet granulation binding agent. From a granulate, obtained in this way, fast-disintegrating tablets, containing e.g. phenoxymethylpenicillin (as the acid) can be prepared. DE-A-2551249 discloses tablets, containing the water soluble β-lactam antibiotic phenoxymethylpenicillin potassium. Although the inventors state that they have solved the problem of making fast-disintegrating tablets containing a high amount of a water soluble drug by using two different granulates (one containing phenoxymethylpenicillin potassium and a disintegrant and the other one containing a disintegrant only), the tablets are said to disintegrate in water and artificial gastric juice only after several minutes. In Example 2 of DE-A-2551249 tablets, containing 93 wt % of phenoxymethylpenicillin potassium and 3.5 wt % of maize starch, are disclosed. The tablets are said to disintegrate in water and artificial gastric juice after not more than 5–6 minutes. NL-A-6911804 discloses effervescent tablets, containing a water soluble β-lactam antibiotic. Although this type of tablets should dissolve in water within a few minutes, they are not suitable for oral administration without dissolving the tablets in water first. FR-A-2320731 discloses fast-disintegrating capsules, containing an orally administrable penicillin or cephalosporin, including hydrates and salts thereof, and 1–8 wt % of cross-linked polyvinylpyrrolidone. The disintegration time of such capsules, containing amoxicillin trihydrate and ampicillin trihydrate, according to the only examples shown, was between 2 and 3.5 minutes. The best result was obtained, using amoxicillin trihydrate as the antibiotic and 3 wt % of intragranular cross-linked polyvinylpyrrolidone.

Another problem associated with oral dosage-forms, containing β-lactam antibiotics, relates to the taste of the same compounds. It has appeared to be very difficult to mask the bad taste (acid or salty and bitter) of the antibiotics in order to provide an acceptable dosage-form for the patients, in particular children. Often large amounts of sugars or related polyhydroxy compounds, sweetening agents and flavours have to be used.

Although water soluble β-lactam antibiotics are used for the treatment of infections already for many decades, there still is a demand for pharmaceutically acceptable quickly dispersible dosage-forms for oral administration, in particular tablets, which can be swallowed as a whole or taken as a suspension, obtained after dispersing the dosage-form in water. The dosage-forms at the same time should have an acceptable taste and/or after-taste, to be arrived at preferably without using substantial amounts of sugars and sodium-containing sweetening agents.

SUMMARY OF THE INVENTION

A granulate, containing 50–99.9 wt % of a water soluble β-lactam antibiotic, 0–50 wt % of a cellulose product, which is microcrystalline cellulose, microfine cellulose or a mixture thereof, and 0–0.5 wt % of a wet granulation binding agent, is provided.

A process for the preparation of a granulate, comprising a water soluble β-lactam antibiotic, is disclosed which process includes moistening components for the granulate with an essentially aqueous liquid without using a substantial amount of a wet granulation binding agent (0–0.5 wt %) and consecutively screening the wet and dry granules through an at least 0.71 mm sieve.

The granulates are advantageously blended with a cellulose product, which is microcrystalline cellulose, microfine cellulose or a mixture thereof, and one or more disintegrants for use in quickly dispersible oral dosage-forms, when placed in an aqueous environment. The taste of the said oral dosage-forms is improved by using a combination of sweetening agents and flavour.

A process for preparing the above dosage-forms is also provided.

DETAILED DESCRIPTION OF THE INVENTION

Water-soluble β-lactam antibiotics, which are absorbed from the gastrointestinal tract after oral administration, belong to the groups of penicillins, cephalosporins, carbapenems, monobactams and cefamycines. In general the said antibiotics are soluble in water only in a salt form, but there are some exceptions. The salts useful in this respect are in particular the alkaline metal and acid addition salts. If more than one group in the antibiotic molecule is available for salt-formation, mono- as well as di-salts may also be useful. As alkaline metal salts the potassium and sodium salts are preferred. As acid addition salts hydrochloric acid salts are preferably used. Specific examples of water soluble orally active β-lactam antibiotics include bacampicillin hydrochloride, carbenicillin sodium, carindacillin sodium, ciclacillin, clometocillin potassium, cloxacillin sodium, dicloxacillin sodium, flucloxacillin sodium, hetacillin potassium, nafcillin sodium, oxacillin sodium, pheneticillin potassium, phenoxymethylpenicillin potassium, phenoxymethylpenicillin sodium, pivampicillin hydrochloride, pivmecillinam hydrochloride, propicillin potassium and talampicillin hydrochloride. Preferred water soluble salts of β-lactam antibiotics are pheneticillin potassium, the sodium and potassium salt of phenoxymethylpenicillin and the sodium salt of flucloxacillin.

According to Martindale, the Extra Pharmacopoeia, 28th edition, 1982, water soluble means that a substance is soluble in water in a ratio of between 1:10 and 1:30. It will be readily apparent that the water soluble β-lactam antibiotics include those which are freely soluble in water (in a ratio between 1:1 and 1:10) and very soluble (in a ratio of 1:<1).

The granulate may essentially consist of the β-lactam antibiotic or may contain the β-lactam antibiotic in admixture with commonly used excipients, such as a cellulose product, which is microcrystalline cellulose, microfine cellulose or a mixture thereof, or an intragranular disintegrant. Advantageously the granulate contains 50–99.9 wt % of the antibiotic. In particular when high doses of an antibiotic have to be incorporated in a swallowable oral dosage-form, the use of large amounts of excipients should be avoided as much as possible. Preferred concentrations of antibiotic in the granulate are at least 70 wt %, but more preferably at least 85 wt %.

The granulate is prepared at room temperature by a wet granulation technique, using an essentially aqueous liquid as the granulation liquid, however without using substantial amounts of wet granulation binding agents. The granulation liquid may contain up to 10 wt % of ethanol, but preferably it consists of water only, in which up to 0.5 wt %, preferably 0.1 wt %, of a wet granulation binding agent may be dissolved, the percentages based on the granulate. Suitable wet granulation binding agents include water soluble celluloses, such as hydroxypropyl celluloses and sodium carboxymethyl cellulose, starches (soluble, pregelatinised), polyvinylpyrrolidone, although naturally occurring binders, such as acacia gum and corn starch, or sugars and polyhydroxy compounds can also be used.

The amounts of granulating liquid to be used may range from 20–35 wt %, preferably from 12.5–20 wt %. Most preferably about 15 wt % is used, the percentages being calculated on the weight of the antibiotic. The granulate can be prepared by gradually adding the essentially aqueous solution comprising 0–0.5 wt % of the wet granulation binding agent to the β-lactam antibiotic and optionally excipients and mixing the mass during 15 to 25 minutes, preferably 20 minutes, and subsequently screening the wet mass thus obtained through a 2.0 mm sieve. After drying the granules in a fluidised bed dryer at an inlet air temperature of between 30 and 60° C., preferably 45° C., they are screened again, but now through a sieve having pores of at least 0.71 mm, but preferably between 1.00 and 1.50 mm. Alternatively, the granules can be milled, e.g. in a hammer mill. The particle size distribution of the granulate, as well as that of the antibiotic, should meet special requirements if the granulate is intended for incorporating in tablets. A suitable distribution is e.g.:

≧–1.400 mm 0.3%
1.000–1.400 mm 28.2%
0.710–1.000 mm 23.8%
0.500–0.710 mm 20.2%
0.355–0.500 mm 12.7%
0.250–0.355 mm 7.6%
0.180–0.250 mm 3.6%
0.125–0.180 mm 2.3%
0.090–0.125 mm 0.8%

Suitable apparatus for production of the granulate include a planetary mixer, but also a fluid bed granulator and a high shear mixer. It has been observed that the optimal mixing time depends on the apparatus used, the mixing speed and the particle size of the powders to be granulated. In case a high speed mixer is used a considerable reduction of mixing times could be achieved.

The granulate obtained shows satisfactory flow properties. Dissolution studies revealed a fast dissolution of the drug, in artificial gastric juice as well as in water. It is another advantage that an organic solvent, with all safety and environment hazards, as granulating liquid can be avoided. Furthermore it has been observed that the taste of the granules can be relatively easily improved by means of the addition of sweetening agents and flavours. Panel tests, performed on volunteers, have shown that taste-making of a water soluble β-lactam antibiotic, such as phenoxymethylpenicillin potassium, in granular form is not more of a problem than the taste-masking of granulates containing a slightly soluble form of the same antibiotic (phenoxymethylpenicillin). It is advantageous that a granulate, containing a water soluble drug for the greater part, can be obtained by a wet granulation technique using an essentially aqueous liquid as the granulation liquid especially since normally a liquid in which the powders to be granulated are only slightly soluble would be selected as the granulating liquid. Despite the fact that the solubility of a compound in the granulating liquid is high and the powder which is in contact with the granulating liquid will dissolve in it, it has been possible to evenly distribute the liquid throughout the powder. Overwetting of the powders to be granulated could be prevented as well as the formation of very hard string-shaped granules after wet screening and drying, which granules are not suitable for compression into tablets. Furthermore, it is an advantage that the wet screening process proceeds very smoothly because the pores of the screen will not gradually silt up.

For obtaining quickly dispersible oral dosage-forms the water soluble β-lactam antibiotic in a granular form is blended with a cellulose product, which is microcrystalline cellulose, microfine cellulose or a mixture thereof, one or more disintegrants, and optionally sweetening agents, flavours and aromas, lubricants, anti-adhesives, flow-promotors etc.

The total percentage of antibiotic and cellulose product is about 85 wt %, the percentage based on the final dosage-form. Although the ratio of antibiotic and cellulose product can be varied, the preferred ratio is about 1:1.

The cellulose product can have a means particle size ranging from 50 to 250 μm, but preferably a product having a mean particle size of 100 μm, such as the microcrystalline cellulose type Avicel® PH 102, is used. If a reduction of the height of the compressed dosage-form is aimed at, the cellulose product can be partially substituted by a calcium phosphate, which is commercially available under the trade name Emcompress®. However, an increase of the disintegration time of such compressed dosage-forms has been observed.

The disintegration time of solid oral dosage-forms according to the invention, such as capsules and tablets, is preferably determined by means of a disintegration time apparatus, operated without using discs e.g., according to the European or British Pharmacopoeia (ERWEKA). The maximal disintegration time of the dosage-forms according to the invention is 2 minutes, but preferably less than one minute. It is also possible to determine a dispersion time, especially of sachet-formulations, in a beaker. Furthermore, dispersible tablets should also meet the requirements of the European or British Pharmacopoeia for such tablets.

Useful disintegrants appear to be among others super disintegrants and include modified starches, cross-carmellose, sodium carboxymethyl cellulose, cross-linked polyvinylpyrrolidone, cross-linked sodium carboxymethyl cellulose, an ion exchange resin such as Amberlite® IRP 88 and low-substituted hydroxypropylcellulose. The said disintegrants, alone or in combination, can be advantageously used in the dosage-forms in order to let these quickly disperse when placed in an aqueous environment.

The disintegrant or mixture of disintegrants is generally used in a concentration between 6 and 15 wt %, the percentage based on the dosage-form. However, preferably 8 wt % is used.

The granular form of the water-soluble β-lactam antibiotic, to be used in the dosage-forms, can be obtained according to the process, as described above. However, in case of very bitter compounds it may be useful to add a filmcoating to the granules, containing the water soluble β-lactam antibiotic. This can be done after preparing the granulate as described above, but it is also possible during the granulating process. Film-forming polymers are e.g. cellulose derivatives and acrylic acid based polymers. Due to the solubility characteristics of the last mentioned commercially available film-forming agents usually no aqueous liquid can be used as the solvent. Advantageous results have been obtained with granulates, prepared by the wet granulation technique, using an alcoholic solution of film-forming polyacrylates, such as Eudragit® E100. On applying an aqueous dispersion of film-forming polyacrylates, such as Eudragit® E30D and RL30D, the granulation and filmcoating process can be combined. The concentration of the film-forming agent in the dosage-form may be up to 5 wt %. Granulates can be prepared with aqueous solutions containing up to 5 wt %, but preferably up to 0.5 wt %, the percentage based on the dosage-form, of the film-forming cellulose derivatives such as hydroxyethyl cellulose, hydroxypropyl cellulose, hydroxypropylmethyl cellulose and sodium carboxymethyl cellulose. The β-lactam antibiotic in granular form, obtained according to any of the methods described above, should have the same characteristics with respect to particle size and flow-properties, as the granulates, prepared by the process, using an aqueous solution containing no substantial amount of wet granulation binding agent.

The dosage-forms according to the present invention are very versatile in that they can be used for the preparation of quickly dispersible and/or disintegrating capsules, tablets, sachet-presentations etc. The bioavailability of the antibiotic from the dosage-form, when dispersed in water prior to administration or swallowed as such, is similar. As already mentioned the taste of the β-lactam antibiotics can be relatively easily masked by a careful selection of sweetening agents and flavours. Sugars or polyhydroxy compounds are no longer required.

Although the foregoing invention has been described in some detail by way of illustration and example for purposes of clarity and understanding, it will be readily apparent to those of ordinary skill in the art in the light of the teachings of this invention that certain changes and modifications may be made thereto without departing from the spirit and the scope of the appended claims.

The following examples further illustrate the invention.

EXAMPLES

Example 1

Preparation of a granulate consisting of phenoxymethylpenicillin potassium 800 g of phenoxymethylpenicillin potassium were granulated at room temperature with 120 ml of water during about 25 minutes in a planetary mixer (HOBART). Thereafter, the wet mass was screened through a 2.0 mm sieve. The granulate was subsequently dried in a fluid bed dryer (RETSCH) during 35 minutes at an inlet air temperature of 45° C. Then, the dry product was screened in an oscillating granulator (FREWITT), equipped with a 1.25 mm sieve.

Results of the cumulative sieve analysis of the granulate:

≧1.000 mm 21%
≧0.710 mm 55%
≧0.500 mm 81%
≧0.355 mm 91%
≧0.250 mm 96%
≧0.180 mm 98%
≧0.125 mm 99%
≧0.090 mm 100%
≧0.090 mm 0%

Example 2

Preparation of a granulate containing phenoxymethylpenicillin potassium 200 g of phenoxymethylpenicillin potassium were granulated with 30 ml of a solution containing 5% or soluble starch (Paselli® SA-2) in a planetary mixer during 20 minutes. After screening the wet mass through a 2.0 mm sieve and drying the product so obtained during 35 minutes in a fluidised bed dryer at an inlet air temperature of 45° C., the granulating procedure was repeated. After drying the product obtained in the second granulating procedure, the granulate was screened in an oscillating granulator equipped with a 1.0 mm sieve.

Example 3

Preparation of a granulate containing phenoxymethylpenicillin potassium and microcrystalline cellulose 366 g of phenoxymethylpenicillin potassium and 152 g of microcrystalline cellulose were mixed in a planetary mixer. Thereafter the mixture was granulated with 125 ml of water during 20 minutes. After screening the wet mass through a 2.0 mm sieve and drying the product thus obtained during 35 minutes in a fluid bed dryer at an inlet air temperature of 45° C., the granules were screened in an oscillating granulator, equipped with a 1.25 mm sieve.

Example 4

Preparation of a granulate consisting of phenoxymethylpenicillin potassium 4000 g of phenoxymethylpenicillin potassium were granulated with 550 ml of water in a high speed mixer operated at 200 rpm during periods between 55 and 120 seconds. Thereafter, the wet mass was screened through a 2.0 mm sieve. The granulation was dried in a fluid bed dryer at an inlet air temperature of 45° C. during 35 minutes. The dry product was screened through a 1.0 mm sieve.

Example 5

Composition and manufacturing method of tablets containing phenoxymethylpenicillin potassium phenoxymethylpenicillin potassium 43.40%

Eudragit® E100 1.74%

Avicel® PH 102 39.0% crosslinked polyvinylpyrrolidone 7.84% saccharin 0.70% aspartame 4.67%

Aerosil® 200V 0.12%

Peppermint flavour 4.94% magnesium stearate 0.39%

768 g of phenoxymethylpenicillin potassium were granulated and moistened with a solution containing 32 g of Eudragit® E100 in 300 ml of ethanol (96%) during about 25 minutes in a planetary mixer. Thereafter the wet mass was screened through a 2.0 mm sieve and dried in a fluid bed drying during 15 minutes at a temperature of 30° C. and subsequently during 10 minutes at a temperature of 45° C. The dried product was screened through a 0.71 mm sieve in an oscillating granulator.

The granules, obtained in the above-described way, were blended with Avicel® PH 102, crosslinked polyvinylpyrrolidone, saccharin, aspartame, peppermint flavour MC 92505 (obtained from Quest), silicon dioxide in a planetary mixture during 10 minutes. Thereafter magnesium stearate was added to the blend and mixing was continued for another three minutes. From the tableting mixture oval tablets were compressed, having a mean weight of 1848 mg. The tablets disintegrated in water within 21 seconds. Friability of the tablets was 0.98% and the mean hardness 12.5 kp.

Example 6

Composition of tablet containing phenoxymethylpenicillin potassium phenoxymethylpenicillin potassium (as 100%) 800.0 mg microcrystalline cellulose 730.4 mg cross-linked polyvinylpyrrolidone 145.6 mg saccharin 13.0 mg aspartame 86.6 mg peppermint aroma 36.2 mg silicon dioxide 2.2 mg magnesium stearate 11.0 mg Example 7

Bioavailability of tablets according to example 5 and 6 in comparison to a commercially available film-coated tablet Intact or dispersed tablets, containing 800 mg of phenoxymethylpenicillin potassium according to example 5 and 6 respectively, and a 780 mg phenoxymethylpenicillin potassium-containing film-coated tablet were tested in five healthy male subjects according to a 5×5 latin square cross-over design. Relative bioavailabilities were assayed by comparing area under the curves, $t_{max}$ and $C_{max}$-values and mean residence times (MRT) of the antimicrobially active compound in plasma. The tablets according to example 5 and 6 gave a relative fast uptake of drug ($t_{max}$ 15–45 min; $C_{max}$ 6–15 mg/ml), and the extent of absorption was comparable to the values of the commercially available film-coated tablet.

The results of this study indicate comparable bioavailabilities of the tablets according to example 5 and 6 and the film-coated reference table, the performance of the latter being in excellent agreement with literature data.

We claim:

1. A process for the preparation of a granulate comprising an orally active β-lactam antibiotic having a solubility in water of 1:≦10, the process comprising:

(a) moistening the antibiotic with an aqueous solution containing 0–0.5 wt % of a wet granulation binding agent the percentage based on the granulate;

(b) screening the mass through a 2 mm sieve;

(c) drying the product obtained in part b; and (d) screening the dry product of part (c) through an at least 0.71 mm sieve using 10–35%, based on the weight of the antibiotic, of the aqueous solution.

2. A process for the preparation of a fast-disintegrating oral dosage-form containing an orally active β-lactam antibiotic having a solubility in water of 1:≦10, the process comprising:

(a) blending the granulate obtained according to the process of claim 1 with i) microcrystalline cellulose, microfine cellulose or a mixture thereof, (ii) one or more disintegrants, and optionally one or more sweetening agents, flavours and other excipients; and (b) compressing the mixture of part (a) or filling it into a capsule or a sachet.

3. The process according to claim 1, wherein the antibiotic is moistened with an aqueous solution containing 0–0.1 wt % of a wet granulation binding agent and the dry product of parts is screened using 12.5–20%, based on the weight of the antibiotic, of the aqueous solution.

* * * * *